(12) United States Patent
Iizuka

(10) Patent No.: US 6,520,677 B2
(45) Date of Patent: Feb. 18, 2003

(54) ANGIOGRAPHY/CT METHOD AND APPARATUS

(75) Inventor: Senichi Iizuka, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 249 days.

(21) Appl. No.: 09/751,698

(22) Filed: Dec. 29, 2000

(65) Prior Publication Data

US 2001/0007588 A1 Jul. 12, 2001

(30) Foreign Application Priority Data

Jan. 7, 2000 (JP) .......................................... 2000-001443

(51) Int. Cl.[7] ................................................. A61B 6/04
(52) U.S. Cl. ......................... 378/209; 378/195; 378/20
(58) Field of Search ................................. 378/209, 195, 378/196, 197, 20, 208; 600/411, 427, 4

(56) References Cited

U.S. PATENT DOCUMENTS

| | | | | |
|---|---|---|---|---|
| 5,367,554 A | * | 11/1994 | Kobayashi et al. | 378/196 |
| 5,960,054 A | * | 9/1999 | Freeman et al. | 378/4 |
| 6,302,579 B1 | * | 10/2001 | Meyer et al. | 378/196 |
| 6,435,713 B1 | * | 8/2002 | Iizuka | 378/195 |

* cited by examiner

*Primary Examiner*—Drew A. Dunn
*Assistant Examiner*—Irakli Kiknadze
(74) *Attorney, Agent, or Firm*—Moonray Kojima

(57) ABSTRACT

In order to effectively use an angiography arm and a CT gantry and improve examination efficiency, angiographic imaging of a subject Ha in an angiography room Ra and CT imaging of a subject Hc in a CT room Rc are independently performed in one mode. In another, a CT gantry 40 is moved to the angiography room Ra with an X-ray protection door D open, to alternately perform angiographic imaging and CT imaging on the subject Ha in the angiography room Ra in a cycle of, for example, five minutes.

20 Claims, 4 Drawing Sheets

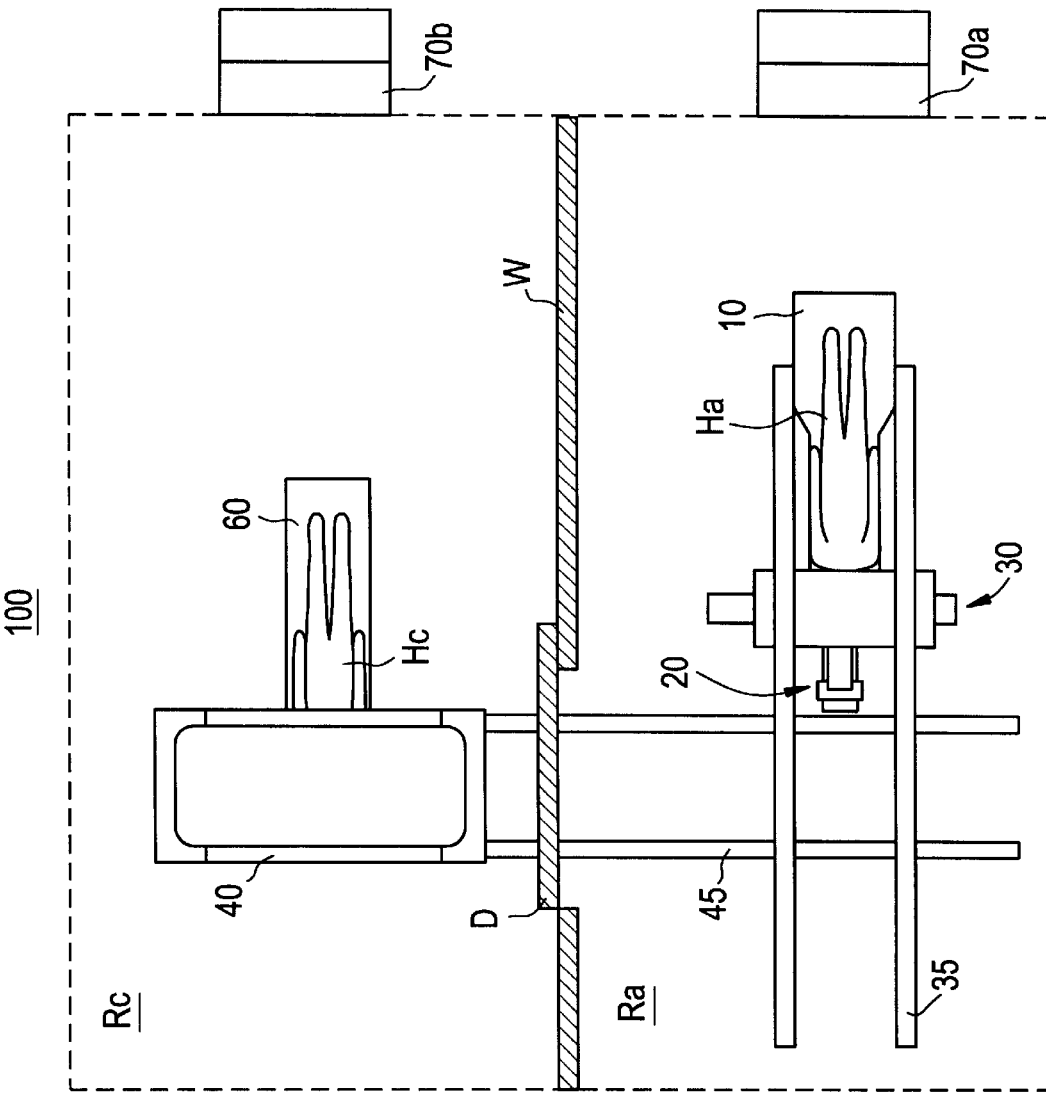

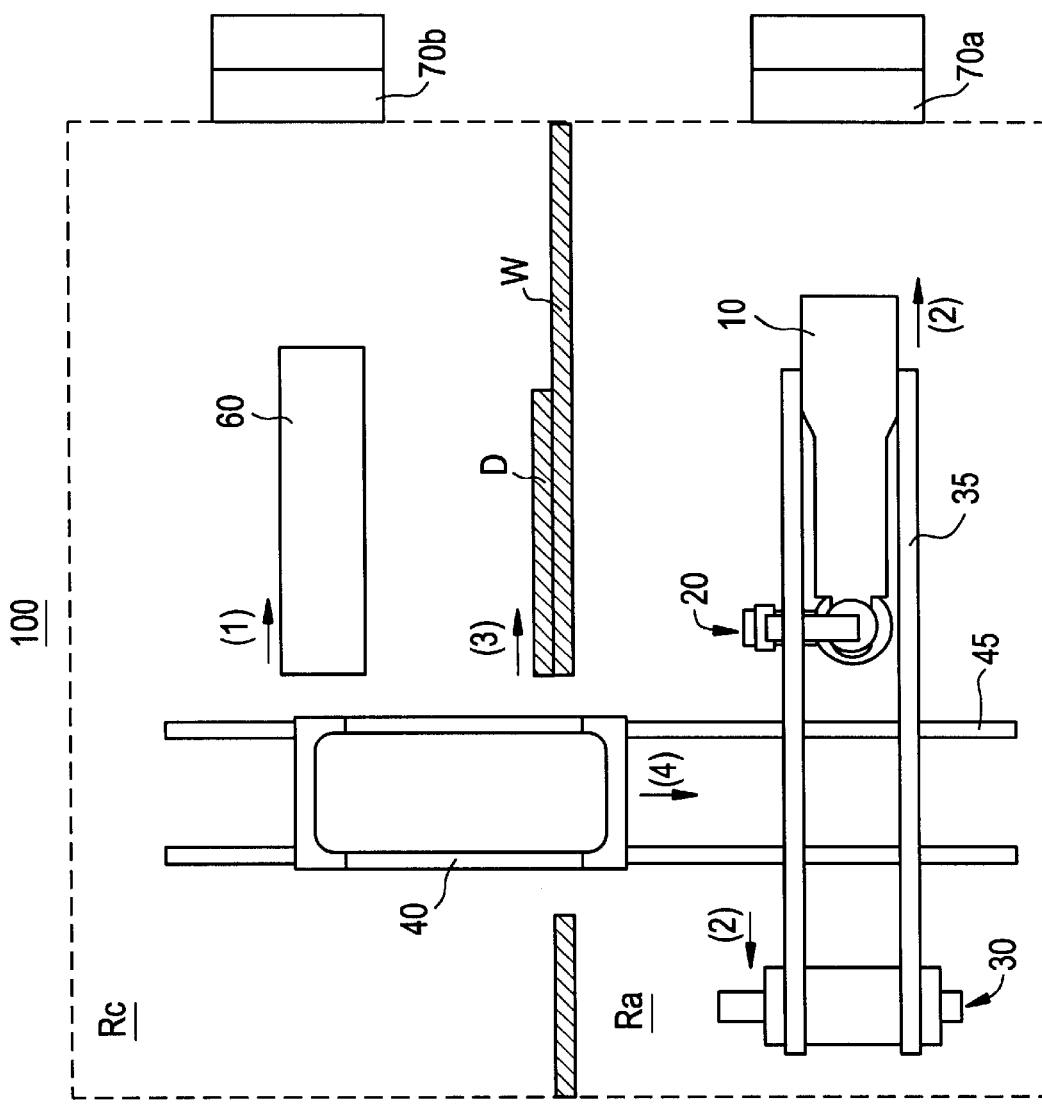

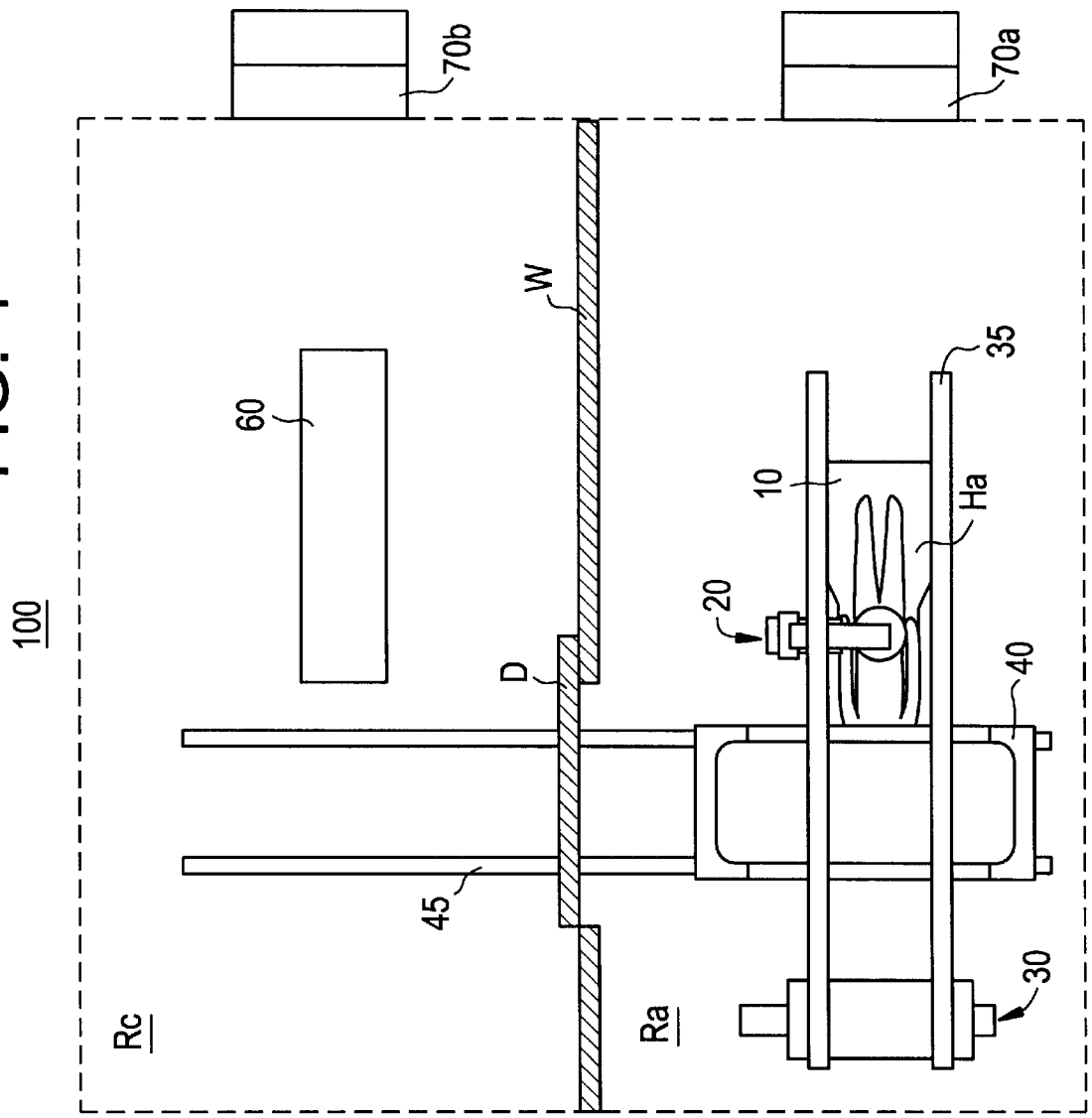

ANGIOGRAPHY/CT METHOD AND APPARATUS

BACKGROUND OF THE INVENTION

The present invention relates to an angiography/CT method and apparatus, and more particularly to an angiography/CT method and apparatus which can effectively use an angiography arm for angiographic imaging and a CT gantry for CT imaging, and can improve examination efficiency.

European Patent Laid Open No. EP0919185A1 discloses an angiography/CT apparatus comprising a top plate for laying a subject, a frontal arm comprising an X-ray tube and an X-ray image receiving device for performing angiographic imaging vertically across the subject laid on the top plate, a CT gantry comprising an X-ray tube and an X-ray detector for performing CT imaging on the subject laid on the top plate, and top plate moving means which allows the top plate to horizontally move in its longitudinal direction.

According to this angiography/CT apparatus, the angiographic imaging is achieved in a frontal plane by moving the top plate to the position of the frontal arm using the top plate moving means. The CT imaging is achieved by moving the top plate to the position of the CT gantry using the top plate moving means. Therefore, angiographic imaging and CT imaging can be alternately performed in a cycle of, for example, five minutes, by alternately moving the top plate between the two positions.

The conventional angiography/CT apparatus cannot however position a subject in the CT gantry while performing angiographic imaging on another subject using the frontal arm, and cannot position a subject at the frontal arm while performing CT imaging on another subject using the CT gantry. Thus, when only angiographic imaging is performed, only the frontal arm is used and the CT gantry is not used at all. On the other hand, when only CT imaging is performed, only the CT gantry is used and the frontal arm is not used at all.

This means that the CT gantry cannot be used in spite of the presence of subject requiring CT imaging without angiographic imaging, so the expensive CT gantry is not effectively used. Similarly, the frontal arm cannot be used in spite of the presence of a subject requiring angiographic imaging without CT imaging, so the expensive frontal arm is not effectively used.

SUMMARY OF THE INVENTION

It is therefore an object of the present invention to provide an angiography/CT method and apparatus in which an angiography arm and a CT gantry can be independently used for different subjects and which can thus effectively use the angiography arm and the CT gantry and can improve examination efficiency.

In accordance with a first aspect of the invention, there is provided an angiography/CT apparatus comprising: an angiography top plate for laying a subject of angiography; an angiography arm comprising an X-ray tube and an X-ray image receiving device for performing angiographic imaging across the subject laid on the angiography top plate; a CT top plate for laying a subject of CT; a CT gantry comprising an X-ray tube and an X-ray detector for performing CT imaging on the subject laid on the CT top plate; and moving means for moving the angiography top plate, angiography arm, CT top plate or CT gantry to enable CT imaging of the subject laid on the angiography top plate using the CT gantry or to enable angiographic imaging of the subject laid on the CT top plate using the angiography arm.

The angiography/CT apparatus of the first aspect has an angiography top plate and a CT top plate which are separate of each other and allow angiographic imaging and CT imaging to be performed independently. Further, since the use of the moving means allows CT imaging using the angiography top plate or angiographic imaging using the CT top plate, angiographic imaging and CT imaging may be alternately performed on a subject laid on, for example, the angiography top plate in a cycle of five minutes, as in the conventional angiography/CT apparatus. Therefore, the angiography arm and the CT gantry can be effectively used and examination efficiency can be improved.

Also in accordance with the first aspect, there is from another viewpoint provided an angiography/CT method comprising the steps of: moving an angiography top plate, angiography arm, CT top plate, or CT gantry; and performing CT imaging on a subject laid on the angiography top plate using the CT gantry or performing angiographic imaging on a subject laid on the CT top plate using the angiography arm.

In accordance with a second aspect, there is provided the angiography/CT apparatus of the first aspect, wherein the angiography top plate and the angiography arm are placed in an angiography room, the CT top plate and the CT gantry are placed in a CT room, and the moving means enables the angiography top plate, angiography arm, CT top plate or CT gantry to be moved between the angiography room and the CT room.

Since the angiography room and the CT room are separately provided in the angiography/CT apparatus of the second aspect, angiographic imaging and CT imaging can be independently performed with one subject in the angiography room and another subject in the CT room completely isolated. Moreover, since CT imaging can be performed in the angiography room or angiography imaging can be performed in the CT room, angiographic imaging and CT imaging may be alternately performed on a subject laid on, for example, the angiography top plate in a cycle of five minutes, as in the conventional angiography/CT apparatus. Therefore, the angiography arm and the CT gantry can be effectively used and examination efficiency can be improved.

In accordance with the second aspect, there is from another viewpoint provided an angiography/CT method, wherein an angiography top plate and an angiography arm are placed in an angiography room, and a CT top plate and a CT gantry are placed in a CT room, the method comprising moving the angiography top plate, angiography arm, CT top plate or CT gantry between the angiography room and the CT room.

In accordance with a third aspect, there is provided the angiography/CT apparatus of the second aspect, wherein the angiography room and the CT room are adjacent to each other across a boundary wall, an electrically driven X-ray protection door is provided in the boundary wall between the rooms, and the angiography top plate, angiography arm, CT top plate or CT gantry is movable between the angiography room and the CT room with the electrically driven X-ray protection door open.

Since the angiographic room and the CT room are adjacent to each other in the angiography/CT apparatus of the third aspect, the moving distance and time are minimized. Moreover, since an electrically driven X-ray protection door is provided, one subject in the angiography room and another subject in the CT room can be completely isolated except at the time of moving. Moreover, unnecessary X-ray exposure can be prevented.

In accordance with the third aspect, there is from another viewpoint provided an angiography/CT method, wherein an angiography room and a CT room are adjacent to each other across a boundary wall and an electrically driven X-ray protection door is provided in the boundary wall between the rooms, the method comprising moving the angiography top plate, angiography arm, CT top plate or CT gantry between the angiography room and the CT room with the electrically driven X-ray protection door open.

In accordance with a fourth aspect, there is provided the angiography/CT apparatus of the third aspect, wherein the angiography top plate and the CT top plate are parallel to the boundary wall in their longitudinal directions, and the moving means moves the CT gantry perpendicular to the boundary wall.

The CT gantry is wide across the front and narrow across its lateral sides. A subject enters from the front.

Since the CT gantry can be moved in a direction perpendicular to its lateral side in the angiography/CT apparatus of the fourth aspect, the width of the electrically driven X-ray protection door can be small, which is advantageous in isolating the angiography room and the CT room.

In accordance with the fourth aspect, there is from another viewpoint provided an angiography/CT method, wherein an angiography top plate and a CT top plate are parallel to a boundary wall in their longitudinal directions, the method comprising moving a CT gantry perpendicular to the boundary wall.

In accordance with a fifth aspect, there is provided an angiography/CT apparatus comprising: an angiography top plate for laying a subject of angiography; a frontal arm comprising an X-ray tube and an X-ray image receiving device for performing angiographic imaging vertically across the subject laid on the angiography top plate; a lateral arm comprising an X-ray tube and an X-ray image receiving device for performing angiographic imaging horizontally across the subject laid on the angiography top plate; a CT top plate for laying a subject of CT; a CT gantry comprising an X-ray tube and an X-ray detector for performing CT imaging on the subject laid on the CT top plate; and moving means for moving the angiography top plate, frontal arm, lateral arm, CT top plate or CT gantry to enable CT imaging of the subject laid on the angiography top plate using the CT gantry or to enable angiographic imaging of the subject laid on the CT top plate using the frontal or lateral arm.

The angiography/CT apparatus of the fifth aspect has an angiography top plate and a CT top plate which are separate of each other and allow angiographic imaging and CT imaging to be performed independently. Further, since the use of the moving means allows CT imaging using the angiography top plate or angiographic imaging using the CT top plate, angiographic imaging and CT imaging can be alternately performed on a subject laid on, for example, the angiography top plate in a cycle of five minutes, as in the conventional angiography/CT apparatus. Therefore, the angiography arm and the CT gantry can be effectively used and examination efficiency can be improved. Furthermore, by providing the frontal and lateral arms, simultaneous angiographic imaging in the frontal and lateral planes, i.e., biplane angiographic imaging can be performed.

In accordance with the fifth aspect, there is from another viewpoint provided an angiography/CT method comprising the steps of: moving an angiography top plate, frontal arm, lateral arm, CT top plate or CT gantry; and performing CT imaging on a subject laid on the angiography top plate using the CT gantry or performing angiographic imaging on a subject laid on the CT top plate using the frontal or lateral arm.

In accordance with a sixth aspect, there is provided the angiography/CT apparatus of the fifth aspect, wherein the angiography top plate and the frontal and lateral arms are placed in an angiography room, the CT top plate and the CT gantry are placed in a CT room, and the moving means enables the angiography top plate, frontal arm, lateral arm, CT top plate or CT gantry to be moved between the angiography room and the CT room.

Since the angiography room and the CT room are separately provided in the angiography/CT apparatus of the sixth aspect, angiographic imaging and CT imaging can be independently performed with one subject in the angiography room and another subject in the CT room completely isolated. Moreover, since CT imaging can be performed in the angiography room or angiography imaging can be performed in the CT room, angiographic imaging and CT imaging may be alternately performed on a subject laid on, for example, the angiography top plate in a cycle of five minutes, as in the conventional angiography/CT apparatus. Therefore, the angiography arm and the CT gantry can be effectively used and examination efficiency can be improved.

In accordance with the sixth aspect, there is from another viewpoint provided an angiography/CT method, wherein an angiography top plate and frontal and lateral arms are placed in an angiography room, and a CT top plate and a CT gantry are placed in a CT room, the method comprising moving the angiography top plate, frontal arm, lateral arm, CT top plate or CT gantry between the angiography room and the CT room.

In accordance with a seventh aspect, there is provided the angiography/CT apparatus of the sixth aspect, wherein the angiography room and the CT room are adjacent to each other across a boundary wall, an electrically driven X-ray protection door is provided in the boundary wall between the rooms, and the angiography top plate, frontal arm, lateral arm, CT top plate or CT gantry is movable between the angiography room and the CT room with the electrically driven X-ray protection door open.

Since the angiographic room and the CT room are adjacent to each other in the angiography/CT apparatus of the seventh aspect, the moving distance and time are minimized. Moreover, since an electrically driven X-ray protection door is provided, one subject in the angiography room and another subject in the CT room can be completely isolated except at the time of moving. Moreover, unnecessary X-ray exposure can be prevented.

In accordance with the seventh aspect, there is from another viewpoint provided an angiography/CT method, wherein an angiography room and a CT room are adjacent to each other across a boundary wall and an electrically driven X-ray protection door is provided in the boundary wall between the rooms, the method comprising moving the angiography top plate, frontal arm, lateral arm, CT top plate or CT gantry between the angiography room and the CT room with the electrically driven X-ray protection door open.

In accordance with an eighth aspect, there is provided the angiography/CT apparatus of the seventh aspect, wherein the angiography top plate and the CT top plate are parallel to the boundary wall in their longitudinal directions, and the moving means moves the CT gantry perpendicular to the boundary wall.

The CT gantry is wide across the front and narrow across its lateral sides. A subject enters from the front.

Since the CT gantry can be moved perpendicular to its lateral side in the angiography/CT apparatus of the eighth aspect, the width of the electrically driven X-ray protection door can be made smaller, which is advantageous in isolating the angiography room and the CT room.

In accordance with the eighth aspect, there is from another viewpoint provided an angiography/CT method, wherein an angiography top plate and a CT top plate are parallel to the boundary wall in their longitudinal directions, the method comprising moving a CT gantry perpendicular to the boundary wall.

The angiography top plate is preferably vertically movable so the subject can easily climb on and off the angiography top plate.

Moreover, the angiography top plate is preferably horizontally rotatable so the subject can easily climb on and off the angiography top plate.

Furthermore, it is preferred that the frontal arm be configured to swivel around a pivot fixed on the floor, the lateral arm be configured to travel along the ceiling, the CT gantry be configured to travel on the floor, and control means be provided for controlling movement of movable portions so that interference of the frontal and lateral arms with the CT gantry is avoided.

According to the angiography/CT apparatus of the present invention, angiographic imaging and CT imaging can be performed independently on different subjects or alternately on the same subject. Therefore, an angiography arm and a CT gantry can be effectively used and examination efficiency can be improved.

Further objects and advantages of the present invention will be apparent from the following description of the preferred embodiments of the invention as illustrated in the accompanying drawings.

BRIEF DESCRIPTION OF THE DRAWINGS

FIG. 2 is a top plan view illustrating independent angiographic imaging of a subject in an angiography room and CT imaging of another subject in a CT room.

FIG. 3 is a top plan view illustrating movement of a CT gantry from the CT room to the angiography room.

FIG. 4 is a top plan view illustrating alternate angiographic imaging and CT imaging of a subject in the angiography room.

DETAILED DESCRIPTION OF THE INVENTION

Figure 1:
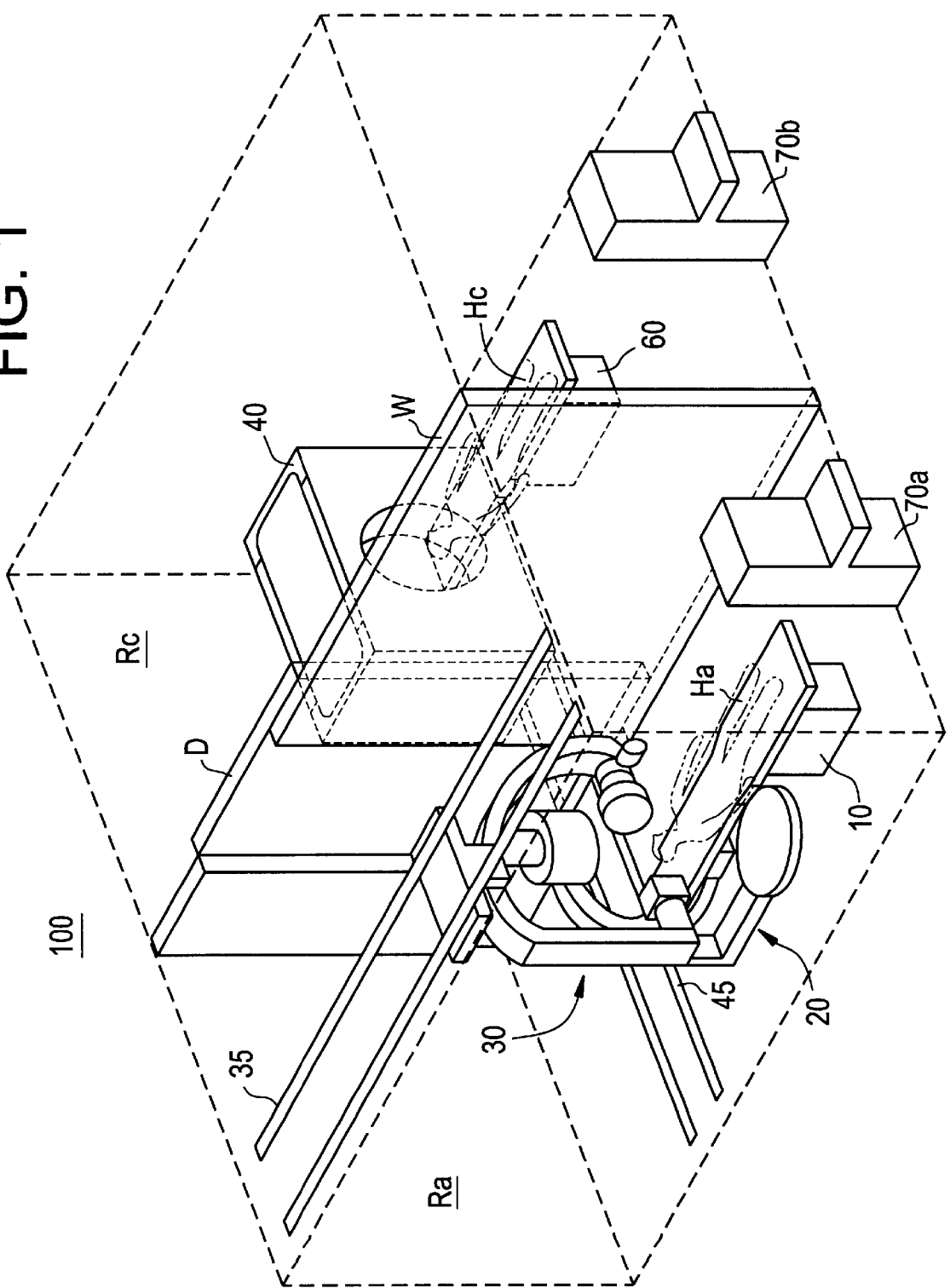
FIG. 1 is a perspective view of a biplane angiography/CT apparatus in accordance with one embodiment of the present invention.

The present invention will now be described in more detail with reference to embodiments shown in the accompanying drawings. It should be noted that the invention is not limited to these embodiments.

FIG. 1 is a perspective view of a biplane angiography/CT apparatus 100 in accordance with one embodiment of the present invention.

The biplane angiography/CT apparatus 100 comprises: an angiography table apparatus 10 for laying a subject of angiography Ha; a frontal arm 20 comprising an X-ray tube and an X-ray image receiving device for performing angiographic imaging vertically across the subject Ha laid on the angiography table apparatus 10; a lateral arm 30 comprising an X-ray tube and an X-ray image receiving device for performing angiographic imaging horizontally across the subject Ha laid on the angiography table apparatus 10; a CT table apparatus 60 for laying a subject of CT Hc; a CT gantry 40 comprising an X-ray tube and an X-ray detector for performing CT imaging on the subject Hc laid on the CT table apparatus 60; a floor rail 45 for moving the CT gantry 40 to allow CT imaging on the subject Ha laid on the angiography table apparatus 10 by the CT gantry 40; a control apparatus 70a for controlling angiographic imaging and CT imaging in an angiography room Ra; and a control apparatus for controlling CT imaging in a CT room Rc.

The angiography table apparatus 10, frontal arm 20, lateral arm 30 and control apparatus 70a are disposed in the angiography room Ra.

The CT table apparatus 60, CT gantry 40 and control apparatus 70b are disposed in the CT room Rc.

The floor rail 45 is extended across the angiography room Ra and the CT room Rc.

The angiography room Ra and the CT room Rc are adjacent to each other across a boundary wall W and an electrically driven X-ray protection door D, both of which can intercept X-rays.

The angiography table apparatus 10 is disposed such that the longitudinal direction of its top plate for laying the subject Ha is parallel to the boundary wall W, and the apparatus 10 can horizontally move the top plate in the longitudinal direction and can vertically move the top plate.

The frontal arm 20 comprises a frontal C arm having opposite ends attached with the X-ray tube and X-ray image receiving device, and an L arm disposed on the floor and capable of horizontally swiveling, for supporting the frontal C arm rotatably along its arc.

The lateral arm 30 comprises a lateral C arm having opposite ends attached with the X-ray tube and X-ray image receiving device, and a runner disposed on the ceiling and capable of traveling along a ceiling rail 35, for supporting the lateral C arm rotatably along its arc. The ceiling rail 35 is extended in a direction parallel to the boundary wall W.

The CT table apparatus 60 is disposed such that the longitudinal direction of its top plate for laying the subject Hc is parallel to the boundary wall W, and the apparatus 60 can horizontally move the top plate in the longitudinal direction and can vertically move the top plate.

With the electrically driven X-ray protection door D open, the CT gantry 40 can be moved in a direction perpendicular to the boundary wall W along the floor rail 45 to be positioned either in the CT room Rc or in the angiography room Ra.

The control apparatus 70a has a monitor function for monitoring the position, angle and height of the top plate of the angiography table apparatus 10, the position and angle of the frontal arm 20, the position and angle of the lateral arm 30, and the position and tilt angle of the CT gantry 40. Thus, the control apparatus 70a interlock-controls the apparatuses and the subjects to maintain safety, and produces alarms and operation guidance as necessary.

The control apparatus 70b has a monitor function for monitoring the position and tilt angle of the CT gantry 40, and interlock-controls the apparatuses and the subjects to maintain safety, and produces alarms and operation guidance as necessary.

FIG. 2 is a top plan view illustrating independent angiographic imaging of the subject Ha in the angiography room Ra and CT imaging on the subject Hc in the CT room Hc.

In the angiography room Ra, angiographic imaging is performed vertically across the subject Ha using the frontal arm 20, and angiographic imaging is performed horizontally across the subject Ha using the lateral arm 30. In this case, the control apparatus 70*a* controls the angiography table apparatus 10, frontal arm 20 and lateral arm 30.

In the CT room Rc, CT imaging is performed on the subject Hc using the CT gantry 40. In this case, the control apparatus 70*b* controls the CT gantry 40.

FIG. 3 is a top plan view illustrating movement of the CT gantry 40 from the CT room Rc to the angiography room Ra.

(1) First, the CT table 60 is retracted to a position not hindering movement of the CT gantry 40 under control of the control apparatus 70*b*. After the retraction, the control apparatus 70*b* issues "CT gantry move permission" to the control apparatus 70*a*.

(2) On the other hand, the angiography table 10 and lateral arm 30 are retracted to a position not hindering movement of the CT gantry 40 under control of the control apparatus 70*a*.

(3) When the retraction of the angiography table 10 and lateral arm 30 is completed and the "CT gantry move permission" has been issued by the control apparatus 70*b*, the control apparatus 70*a* is enabled to open the electrically driven X-ray protection door D in response to an operator instruction.

(4) When the electrically driven X-ray protection door D is completely opened, the control apparatus 70*a* is enabled to move the CT gantry 40 to the angiography room Ra in response to an operator instruction.

(5) After the CT gantry 40 has been moved to the angiography room Ra, the control apparatus 70*a* is enabled to shut the electrically driven X-ray protection door D in response to an operator instruction.

FIG. 4 is a top plan view illustrating alternate angiographic imaging and CT imaging of the subject Ha in the angiography room Ra.

In the angiography room Ra, angiographic imaging can be performed across the subject Ha using the frontal arm 20. At the same time, CT imaging can be performed on the subject Ha using the CT gantry 40. In this case, the control apparatus 70*a* controls the angiography table apparatus 10, frontal arm 20 and CT gantry 40.

Control for moving the CT gantry 40 from the angiography room Ra back to the CT room Rc is the inverse of that shown in FIG. 3.

(1) First, the angiography table 10 is retracted to a position not hindering movement of the CT gantry 40 under control of the control apparatus 70*a*. After the retraction, the control apparatus 70*a* issues "CT gantry move permission" to the control apparatus 70*b*.

(2) On the other hand, the CT table 60 is retracted to a position not hindering movement of the CT gantry 40 under control of the control apparatus 70*b*.

(3) When the retraction of the CT table 60 is completed and the "CT gantry move permission" has been issued by the control apparatus 70*a*, the control apparatus 70*b* is enabled to open the electrically driven X-ray protection door D in response to an operator instruction.

(4) When the electrically driven X-ray protection door D is completely opened, the control apparatus 70*b* is enabled to move the CT gantry 40 to the CT room Rc in response to an operator instruction.

(5) After the CT gantry 40 has been moved to the CT room Rc, the control apparatus 70*b* is enabled to shut the electrically driven X-ray protection door D in response to an operator instruction.

The biplane angiography/CT apparatus 100 affords the following effects:

(1) Angiographic imaging in the angiography room Ra and CT imaging in the CT room Re can be independently performed, or angiographic imaging and CT imaging can be alternately performed in the angiography room Ra in a cycle of, for example, five minutes. Therefore, the frontal and lateral arms 20 and 30 and the CT gantry 40 can be effectively used, and examination efficiency can be improved.

(2) By providing the frontal and lateral arms 20 and 30, simultaneous angiographic imaging in the frontal and lateral planes can be performed.

(3) Angiographic imaging and CT imaging can be independently performed with the subject Ha in the angiography room Ra and the subject Hc in the CT room Rc completely isolated.

(4) Since the angiographic room Ra and the CT room Rc are adjacent to each other, the moving distance and time are minimized. Moreover, since the electrically driven X-ray protection door D is provided, the subject Ha in the angiography room Ra and the subject Hc in the CT room Rc can be completely isolated except at the time of moving. Moreover, unnecessary X-ray exposure can be prevented.

(5) Since the CT gantry 40 can be moved in a direction perpendicular to its lateral side having smaller width, the width of the electrically driven X-ray protection door D can be small, which is advantageous in isolating the angiography room Ra and the CT room Rc.

Other Embodiment

While the CT gantry 40 is moved in the first embodiment, the angiography table 10, frontal arm 20, lateral arm 30 or CT table 60 may be configured to move instead of, or in addition to, moving the CT gantry 40.

Many widely different embodiments of the invention may be configured without departing from the spirit and the scope of the present invention. It should be understood that the present invention is not limited to the specific embodiments described in the specification, except as defined in the appended claims.

What is claimed is:

1. An angiography/CT apparatus comprising:
   an angiography top plate for laying a subject of angiography;
   an angiography arm comprising an X-ray tube and an X-ray image receiving device for performing angiographic imaging across the subject laid on said angiography top plate;
   a CT top plate for laying a subject of CT;
   a CT gantry comprising an X-ray tube and an X-ray detector for performing CT imaging on the subject laid on said CT top plate; and
   moving means for moving said angiography top plate, angiography arm, CT top plate or CT gantry to enable CT imaging of the subject laid on said angiography top plate using said CT gantry or to enable angiographic imaging of the subject laid on said CT top plate using said angiography arm.

2. The angiography/CT apparatus as recited in claim 1, wherein said angiography top plate and said angiography arm are placed in an angiography room, said CT top plate and said CT gantry are placed in a CT room, and said moving means enables said angiography top plate, angiography arm, CT top plate or CT gantry to be moved between said angiography room and said CT room.

3. The angiography/CT apparatus as recited in claim 2, wherein said angiography room and said CT room are adjacent to each other across a boundary wall, an electrically driven X-ray protection door is provided in said boundary wall between said rooms, and said angiography top plate, angiography arm, CT top plate or CT gantry is movable between said angiography room and said CT room with said electrically driven X-ray protection door open.

4. The angiography/CT apparatus as recited in claim 3, wherein said angiography top plate and said CT top plate are parallel to said boundary wall in their longitudinal directions, and said moving means moves said CT gantry perpendicular to said boundary wall.

5. An angiography/CT apparatus comprising:
    an angiography top plate for laying a subject of angiography;
    a frontal arm comprising an X-ray tube and an X-ray image receiving device for performing angiographic imaging vertically across the subject laid on said angiography top plate;
    a lateral arm comprising an X-ray tube and an X-ray image receiving device for performing angiographic imaging horizontally across the subject laid on said angiography top plate;
    a CT top plate for laying a subject of CT;
    a CT gantry comprising an X-ray tube and an X-ray detector for performing CT imaging on the subject laid on said CT top plate; and
    moving means for moving said angiography top plate, frontal arm, lateral arm, CT top plate or CT gantry to enable CT imaging of the subject laid on said angiography top plate using said CT gantry or to enable angiographic imaging of the subject laid on said CT top plate using said frontal or lateral arm.

6. The angiography/CT apparatus as recited in claim 5, wherein said angiography top plate and said frontal and lateral arms are placed in an angiography room, said CT top plate and said CT gantry are placed in a CT room, and said moving means enables said angiography top plate, frontal arm, lateral arm, CT top plate or CT gantry to be moved between said angiography room and said CT room.

7. The angiography/CT apparatus as recited in claim 6, wherein said angiography room and said CT room are adjacent to each other across a boundary wall, an electrically driven X-ray protection door is provided in said boundary wall between said rooms, and said angiography top plate, frontal arm, lateral arm, CT top plate or CT gantry is movable between said angiography room and said CT room with said electrically driven X-ray protection door open.

8. The angiography/CT apparatus as recited in claim 7, wherein said angiography top plate and said CT top plate are parallel to said boundary wall in their longitudinal directions, and said moving means moves said CT gantry perpendicular to said boundary wall.

9. The angiography/CT apparatus as recited in claim 8, wherein said frontal arm is configured to swivel around a pivot fixed on a floor, said lateral arm is configured to travel along a ceiling, said CT gantry is configured to travel on the floor, and control means is provided for controlling movement of movable portions so that interference of said frontal and lateral arms with said CT gantry is avoided.

10. The apparatus of claim 7, wherein said frontal arm is configured to swivel around a pivot fixed on a floor, said lateral arm is configured to travel along a ceiling, said CT gantry is configured to travel on the floor, and control means is provided for controlling movement of moveable portions so that interference of said frontal and lateral arms with said CT gantry is avoided.

11. The apparatus of claim 6, wherein said frontal arm is configured to swivel around a pivot fixed on a floor, said lateral arm is configured to travel along a ceiling, said CT gantry is configured to travel on the floor, and contrl means is provided for controlling movement of moveable portions so that interference of said frontal and lateral arms with said CT gantry is avoided.

12. The apparatus of claim 5, wherein said frontal arm is configured to swivel around a pivot fixed on a floor, said lateral arm is configured to travel along a ceiling, said CT gantry is configured to travel on the floor, and control means is provided for controlling movement of moveable portions so that interference of said frontal and lateral arms with said CT gantry is avoided.

13. An angiography/CT method for use in an angiography/CT apparatus provided with an angiography top plate for laying a subject of angiography, an angiography arm comprising an X-ray tube and an X-ray image receiving device for performing angiographic imaging across the subject laid on said angiography top plate, a CT top plate for laying a subject of CT, and a CT gantry comprising an X-ray tube and an X-ray detector for performing CT imaging on the subject laid on said CT top plate, said method comprising the steps of:
    moving said angiography top plate, aniography arm, CT top plate or CT gantry; and
    performing CT imaging on the subject laid on said angiography top plate using said CT gantry or performing angiographic imaging on the subject laid on said CT top plate using said angiography arm.

14. The angiography/CT method as recited in claim 13, wherein said angiography top plate and said angiography arm are placed in an angiography room and said CT top plate and said CT gantry are placed in a CT room, said method comprising moving said angiography top plate, angiography arm, CT top plate or CT gantry between said angiography room and said CT room.

15. The angiography/CT method as recited in claim 14, wherein said angiography room and said CT room are adjacent to each other across a boundary wall and an electrically driven X-ray protection door is provided in said boundary wall between said rooms, said method comprising moving said angiography top plate, angiography arm, CT top plate or CT gantry between said angiography room and said CT room with said electrically driven X-ray protection door open.

16. The method of claim 15, wherein said angiography top plate and said CT top plate are parallel to said boundary wall in longitudinal directions, said method comprising the step of moving said CT gantry perpendicular to said boundary wall.

17. An angiography/CT method for use in an angiography/CT apparatus provided with an angiography top plate for laying a subject of angiography, a frontal arm comprising an X-ray tube and an X-ray image receiving device for performing angiographic imaging vertically across the subject laid on said angiography top plate, a lateral arm comprising an X-ray tube and an X-ray image receiving device for performing angiographic imaging horizontally across the subject laid on said angiography top plate, a CT top plate for laying a subject of CT, and a CT gantry comprising an X-ray tube and an X-ray detector for performing CT imaging on the subject laid on said CT top plate, said method comprising the steps of:

moving said angiography top plate, frontal arm, lateral arm, CT top plate or CT gantry; and performing CT imaging on the subject laid on said angiography top plate using said CT gantry or performing angiographic imaging on the subject laid on said CT top plate using said frontal and/or lateral arms.

18. The angiography/CT method as recited in claim 17, wherein said angiography top plate and said frontal and lateral arms are placed in an angiography room and said CT top plate and said CT gantry are placed in a CT room, said method comprising moving said angiography top plate, frontal arm, lateral arm, CT top plate or CT gantry between said angiography room and said CT room.

19. The angiography/CT method as recited in claim 18, wherein said angiography room and said CT room are adjacent to each other across a boundary wall and an electrically driven X-ray protection door is provided in said boundary wall between said rooms, said method comprising moving said angiography top plate, frontal arm, lateral arm, CT top plate or CT gantry between said angiography room and said CT room with said electrically driven X-ray protection door open.

20. The angiography/CT method as recited in claim 19, wherein said angiography top plate and said CT top plate are parallel to said boundary wall in their longitudinal directions, said method comprising moving said CT gantry perpendicualr to said boundary wall.

* * * * *